United States Patent [19]

Sakamoto et al.

[11] Patent Number: 5,763,232
[45] Date of Patent: Jun. 9, 1998

[54] METHOD FOR PRODUCING 3-HYDROXY NITROGEN-CONTAINING SIX-MEMBERED CYLIC COMPOUND

[75] Inventors: Takeshi Sakamoto; Yukie Takai; Reiko Sashida; Makoto Ueda, all of Yokohama; Toru Nagasawa, Gifu, all of Japan

[73] Assignee: Mitsubishi Chemical Corporation, Tokyo, Japan

[21] Appl. No.: 798,919

[22] Filed: Feb. 12, 1997

[30] Foreign Application Priority Data

Feb. 15, 1996 [JP] Japan ................................. 8-027844

[51] Int. Cl.⁶ ............................................ C12P 17/12
[52] U.S. Cl. .................. 435/122; 435/121; 435/822; 435/880
[58] Field of Search ...................... 435/121, 122, 435/822, 880

[56] References Cited

U.S. PATENT DOCUMENTS

| | | | |
|---|---|---|---|
| 4,738,924 | 4/1988 | Kulla et al. | 435/121 |
| 5,151,351 | 9/1992 | Hoeks et al. | 435/122 |
| 5,273,893 | 12/1993 | Kiener | 435/122 |
| 5,516,661 | 5/1996 | Kiener | 435/122 |

Primary Examiner—Herbert J. Lilling
Attorney, Agent, or Firm—Wenderoth, Lind & Ponack, L.L.P.

[57] ABSTRACT

A method for producing a 3-hydroxy nitrogen-containing six-membered cyclic compound is provided. Namely, microbial cells of a microorganism and/or a preparation obtained from the microbial cells is allowed to act on a nicotinic acid derivative or a 2-pyrazinecarboxylic acid derivative represented by the following general formula:

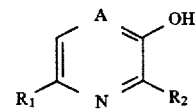

wherein $R_1$ and $R_2$ may be the same or different, representing hydrogen atom, halogen atom, hydroxyl group, amino group, carboxyl group, cyano group, oxime group, or alkyl group having a number of carbon atom or atoms of 1 to 5 respectively, and A represents carbon atom or nitrogen atom, the microbial cells and/or the preparation obtained from the microbial cells having an ability to perform hydroxylation of the nicotinic acid derivative or the 2-pyrazinecarboxylic acid derivative accompanied by decarboxylation of carboxyl group.

6 Claims, No Drawings

METHOD FOR PRODUCING 3-HYDROXY NITROGEN-CONTAINING SIX-MEMBERED CYLIC COMPOUND

BACKGROUND OF THE INVENTION

1. Field of the Invention

The present invention relates to a method for producing a 3-hydroxy nitrogen-containing six-membered cyclic compound based on the use of microbial cells of a microorganism and/or a preparation obtained from the microbial cells. The 3-hydroxy nitrogen-containing six-membered cyclic compound is a substance useful as an intermediate material for producing pharmaceuticals.

2. Description of the Related Art

Many reports have been hitherto made on methods for producing the 3-hydroxy nitrogen-containing six-membered cyclic compound. However, all of the reported methods are based on chemical synthesis. Those hitherto reported include, for example, a method based on heating of 2-acetylfuran in the presence of ammonia (*J. Med. Chem.*, 11, 792 (1968)), a method based on thermal degradation of melanoidine (*Agr. Biol. Chem.*, 40, 2051 (1976)), and a method based on photooxidation of 2-aminomethylfuran under a low temperature condition (*Chem. Pharm. Bull.*, 39, 181 (1991)).

The conventional methods based on chemical synthesis are not necessarily satisfactory to be used as an industrial method because of, for example, the following reasons. Namely, an expensive material is used, an organic solvent containing chlorine is used, and large amounts of impurities are by-produced, causing problems in recovery and purification steps.

SUMMARY OF THE INVENTION

An object of the present invention is to provide a method for industrially and inexpensively producing a 3-hydroxy nitrogen-containing six-membered cyclic compound.

As a result of diligent investigations by the present inventors in order to achieve the object described above, a microorganism capable of producing a 3-hydroxy nitrogen-containing six-membered cyclic compound from nicotinic acid has been found, and thus the present invention has been completed.

Namely, the gist of the present invention lies in a method for producing a 3-hydroxy nitrogen-containing six-membered cyclic compound represented by the following general formula (I):

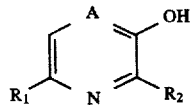

wherein $R_1$ and $R_2$ independently represent hydrogen atom, halogen atom, hydroxyl group, amino group, carboxyl group, cyano group, oxime group, or alkyl group having a number of carbon atom or atoms of 1 to 5 respectively, and A represents carbon atom or nitrogen atom, the method comprising the step of allowing microbial cells of a microorganism and/or a preparation obtained from the microbial cells to act on a nicotinic acid derivative or a 2-pyrazinecarboxylic acid derivative represented by the following general formula (II):

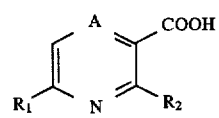

wherein $R_1$, $R_2$, and A are synonymous with those defined in the formula (I), the microbial cells and/or the preparation obtained from the microbial cells having an ability to perform hydroxylation of the nicotinic acid derivative or the 2-pyrazinecarboxylic acid derivative accompanied by decarboxylation of carboxyl group.

According to preferred embodiments of the present invention, there are provided:

(1) a method for producing the 3-hydroxy nitrogen-containing six-membered cyclic compound, comprising the step of allowing microbial cells of a microorganism and/or a preparation obtained from the microbial cells to act on nicotinic acid, the microbial cells and/or the preparation obtained from the microbial cells having an ability to perform hydroxylation of nicotinic acid accompanied by decarboxylation of carboxyl group; and (2) a method for producing the 3-hydroxy nitrogen-containing six-membered cyclic compound, comprising the step of allowing microbial cells of a microorganism and/or a preparation obtained from the microbial cells to act on 6-chloronicotinic acid, the microbial cells and/or the preparation obtained from the microbial cells having an ability to perform hydroxylation of 6-chloronicotinic acid accompanied by decarboxylation of carboxyl group.

The microorganism described above is preferably exemplified by microorganisms belonging to the genus Rhodococcus and the genus Serratia. Especially, microorganisms belonging to the genus Rhodococcus are preferably used in the present invention. The method of the present invention will be explained in detail below.

In the present invention, the nicotinic acid derivative or the 2-pyrazinecarboxylic acid derivative represented by the general formula (II) is used as a raw material. The microbial cells of the specified microorganism or the preparation obtained from the microbial cells is allowed to act on the raw material to produce the 3-hydroxy nitrogen-containing six-membered cyclic compound represented by the general formula (I). The alkyl group having a number of carbon atom or atoms of 1 to 5 represented by $R_1$ and $R_2$ in the formulas includes, for example, methyl group, ethyl group, n-propyl group, iso-propyl group, n-butyl group, iso-butyl group, sec-butyl group, and tert-butyl group. In a preferred embodiment, $R_1$ and $R_2$ represent hydrogen atom or halogen atom, and A represents carbon atom. In an especially preferred embodiment, $R_1$ and $R_2$ represent hydrogen atom and A represents hydrogen atom, or $R_1$, $R_2$ and A respectively represent halogen atom, hydrogen atom and carbon atom in this order.

In the present invention, any microorganism may be used provided that the microorganism has the ability to perform hydroxylation of the nicotinic acid derivative or the 2-pyrazinecarboxylic acid derivative represented by the general Formula (II) accompanied by decarboxylation of carboxyl group. Especially preferred microorganisms include microorganisms belonging to the genus Rhodococcus or the genus Serratia. The microorganism belonging to the genus Rhodococcus or the genus Serratia to be used in the present invention includes, for example, *Rhodococcus rhodochrous* ATCC 14350, *Rhodococcus rhodochrous* ATCC 19150, *Rhodococcus equi* ATCC 21329, Rhodococcus sp. IFO 13161 and Rhodococcus sp. MCI 2956, and *Serratia plymuthica* IAM 13543 and *Serratia marcescens* IAM 12142. All of the bacterium of Rhodococcus sp. MCI 2956 isolated from natural soil will be described below.

1. Morphological characteristics

Microscopical observation was performed after cultivation at 30° C. for 9 hours and 30 hours respectively on heart-infusion agar medium. Cells of MCI 2956 strain elongated irregular at an initial stage of cultivation, and they became to form branched hyphae. After that, the cells underwent fragmentation along with the passage of time, and they became to form short rods or irregular rods. The fragmented cells had no motility. Aerial mycelium, spore, and sporangium were not observed.

2. Cultural characteristics

Properties or situations appeared after cultivation at 30° C. for 10 days on media prescribed in ISP (International Streptomyces Project) are shown in the following Table 1.

TABLE 1

| Medium | Item | MCI 2956 |
| --- | --- | --- |
| Yeast-malt agar (ISP No. 2) | G | good, wrinkled, orange |
| | AM | not formed |
| | SP | not produced |
| Oatmeal agar (ISP No. 3) | G | poor, coarsely granular, orange |
| | AM | not formed |
| | SP | not produced |
| Starch-inorganic salt agar (ISP No. 4) | G | extremely poor, coarsely granular, pale orange |
| | AM | not formed |
| | SP | not produced |
| Glycerol-asparagine agar (ISP No. 5) | G | poor, coarsely granular, dull orange |
| | AM | not formed |
| | SP | not produced |

G: growth, AM: aerial mycelium, SP: soluble pigment.

3. Physiological characteristics

Physiological characteristics of MCI 2956 strain are shown below.

(1) Temperature range for growth: 20° to 40° C.
(2) Liquefaction of gelatin: negative.
(3) Hydrolysis of starch: negative.
(4) Coagulation or peptonization of skim milk: negative.
(5) Formation of melanin-like pigment: negative.
(6) Utilization of carbon sources (cultivation at 30° C. for 14 days on Pridham and Gottlieb agar medium): see the following description.

It was observed that MCI 2956 strain grew a little even on a control medium to which no carbon source was added. However, the control is regarded as (−), and relative assimilation properties thus obtained are shown in Table 2.

TABLE 2

| Carbon source | Growth of MCI 2956 |
| --- | --- |
| L-Arabinose | − |
| D-Fructose | + |
| D-Glucose | + |
| Inositol | − |
| D-Mannitol | + |
| Raffinose | − |
| L-Rhamnose | + |
| Sucrose | + |
| D-Xylose | − |

+: utilizable, ±: slightly utilizable, −: non-utilizable.

4. Chemotaxonomic characteristics

Chemotaxonomic characteristics of MCI 2956 strain are shown in Table 3.

TABLE 3

| Item | MCI 2956 |
| --- | --- |
| (1) Diamino amino acid in cell wall peptideglycan: | meso-diaminopimeric acid |
| (2) sugar in hydrolysate of whole cell: | arabinose, galactose, ribose |
| (3) N-Acyl type of call wall peptideglycan: | glycolyl type |
| (4) Isoprenoid quinone: | MK-8 ($H_2$) |
| (5) Number of carbon atoms of mycolic acid: | 44 to 50 (even-numbered acid and small amount of odd-numbered acid) |
| (6) G + C content in DNA (mole %): | 69.0% |

5. Remarks on taxonomic properties

MCI 2956 strain exhibits polymorphism in its cell cycle. The cells elongate in a branched mycerial form at an initial stage of cultivation. The cells undergo fragmentation along with the passage of time and, they become short rods-shaped or rods-shaped. MCI 2956 strain contains meso-diaminopimeric acid in its cell wall, and it contains arabinose and galactose in its sugar fraction obtained from whole cell. Accordingly, it has been revealed that the type of cell wall of MCI 2956 strain is the IV type. The N-acyl type of cell wall peptideglycan is the glycolyl type. According to these features, it is suggested that MCI 2956 strain belongs to the family Nocardiaceae or to the genus Mycobacterium. It is known that bacteria belonging to these bacterial groups are specifically characterized in that they have mycolic acid (β-hydroxy fatty acid having long-chain alkyl group at α-position) in their cell walls. The respective genera of these bacterial groups are definitely defined according to other chemotaxonomic characteristics.

Thus MCI 2956 strain was compared, for its chemical taxonomical features, with bacteria belonging to the family Nocardiaceae and the genus Mycobacterium described in "The Prokaryotes", 2nd edition (1992), Vol. 2, pp. 1180 to 1270 so that MCI 2956 strain was identified at the level of genus.

Morphological characteristics and chemotaxonomic features of MCI 2956 strain were compared with those of bacterial groups belonging to the family Nocardiaceae and the genus Mycobacterium. Obtained results are shown in Table 4. The cells of MCI 2956 strain elongate to have a branched mycerial form at an initial stage of cultivation. MCI 2956 strain had menaquinone MK-8 ($H_2$), having a number of carbon atoms of mycolic acid of 44 to 50, and G+C content in DNA of 69.0%. As shown in Table 4, these features were well coincident with the features of those belonging to the genus Rhodococcus.

Therefore, the bacterial strain isolated from soil in the present invention, i.e., MCI 2956 has been identified to be Rhodococcus sp.

TABLE 4

| Feature | Mycobacterium | Tsukamurella | Nocardia | Gordona | Rhodococcus | MCI 2956 |
|---|---|---|---|---|---|---|
| Form | rod | rod spherical rod | filamentous ↓ rod spherical formation of aerial mycelium | rod ↓ spherical | filamentous (branched) ↓ rod spherical | filamentous (branched) ↓ rod short rod |
| Predominant menaquinone (MK-) | 9 ($H_2$) | 9 | 8 ($H_4$) | 9 ($H_2$) | 8 ($H_2$) | 8 ($H_2$) |
| Mycolic acid (number of carbons) | 60–90 | 64–78 | 46–60 | 48–66 | 34–52 | 44–50 |
| G + C % in DNA | 62–72 | 67–68 | 64–72 | 63–69 | 67–73 | 69.0 |

In the production method according to the present invention, one or more species of the foregoing microorganisms are used to prepare the microbial cells and/or the preparation obtained from the microbial cells. Specifically, those preferably usable include the microbial cells as they are, obtained by cultivating the microorganism, and the preparation obtained by treating, in accordance with known procedures, the microbial cells obtained by cultivation, i.e., any preparation obtained from the microbial cells, including, for example, those obtained from the microbial cells by means of any treatment based on the use of acetone, lyophilization, and physical or enzymatic disruption. It is also possible to use an enzyme fraction extracted as a crude preparation or a purified preparation from the microbial cells or the preparation obtained from the microbial cells, the enzyme fraction having the ability to act on the carboxyl group of the nicotinic acid derivative or the 2-pyrazinecarboxylic acid derivative represented by the general formula (II) and perform decarboxylation and hydroxylation of the derivative so that the derivative is converted into the 3-hydroxy nitrogen-containing six-membered cyclic compound represented by the general formula (I). It is also possible to use those obtained by immobilizing, for example, the microbial cells, the preparation obtained from the microbial cells, or the microbial strains described above are known except for Rhodococcus sp. MCI 2956. They are easily available from National Institute of Bioscience and Human Technology of Agency of Industrial Science and Technology, Institute for Fermentation, Osaka (IFO), American Type Culture Collection (ATCC), and Institute of Applied Microbiology, the University of Tokyo, Tokyo (IAM) respectively. Rhodococcus sp. MCI 2956 is a bacterium isolated by the present inventors from natural soil. This bacterium was deposited in National Institute of Bioscience and Human Technology of Agency of Industrial Science and Technology (1-3, Higashi 1-chome, tsukuba-shi, ibaraki-ken, 305 Japan) on Jan. 29, 1996, as deposition number of FERM P-15404, and transferred from the original deposition to international deposition based on Budapest Treaty on Feb. 6, 1997, and has been deposited as deposition number of FERM BP-5813. The microorganisms to be used in the present invention may be any strain of any type including, for example, wild strains, mutant strains which are obtained by treatment such as ultraviolet light irradiation, treatment by using of N-methyl-N'-nitro-N-nitrosoguanidine (NTG), ethylmethanesulfonate (EMS), nitrous acid or acridine, and recombinant strains derived in accordance with genetic techniques such as cell fusion and gene recombination. Now, the microbiological features of the enzyme fraction obtained as described above, onto a carrier such as polyacrylamide gel and carageenan gel. Thus the term "microbial cells and/or a preparation obtained from the microbial cells" is herein used as a concept which includes all of the microbial cells the preparation obtained from the microbial cells, the enzyme fraction, and the immobilized preparation thereof described above.

Next, the production method according to the present invention will be specifically explained.

In general, the microorganism is used after cultivation, in the production method according to the present invention. The cultivation can be performed in accordance with an ordinary method. The medium used for the cultivation of the microorganism contains, for example, a carbon source, a nitrogen source, and inorganic ions which can be assimilated by the microorganism. Those appropriately usable as the carbon source include, for example, carbohydrates such as glucose, alcohols such as glycerol, and organic acids. Those appropriately usable as the nitrogen source include, for example, NZ amine, tryptose, yeast extract, and polypeptone. Those optionally and appropriately usable as the inorganic ions include, for example, phosphate ion, magnesium ion, iron ion, manganese ion, and molybdenum ion. Further, it is effective to add vitamins such as inositol, pantothenic acid, and nicotinic acid amide, if necessary. The cultivation is performed for 15 to 100 hours under an aerobic condition while making control within appropriate ranges of pH of about 6 to 8 and a temperature of about 20° to 35° C.

Those usable as the method for producing the 3-hydroxy nitrogen-containing six-membered cyclic compound by allowing the microorganism to act on the nicotinic acid derivative or the 2-pyrazinecarboxylic acid derivative represented by the general formula (II) include, for example, a method comprising cultivating the microorganism, adding the nicotinic acid derivative or the 2-pyrazinecarboxylic acid derivative represented by the general formula (II) to an obtained microbial cell suspension, and making a reaction to obtain 3-hydroxy nitrogen-containing six-membered cyclic compound, a method comprising adding the nicotinic, acid derivative or the 2-pyrazinecarboxylic acid derivative represented by the general formula (II) to a medium, and simultaneously performing cultivation and a reaction, and a method comprising adding the nicotinic acid derivative or the 2-pyrazinecarboxylic acid derivative represented by the general formula (II) after completion of cultivation to further perform a reaction. The reaction temperature is preferably 15° to 40° C., and the reaction is preferably performed in a range of pH 5 to 10. The concentration of the nicotinic acid derivative or the 2-pyrazinecarboxylic acid derivative represented by the general formula (II) is desirably in a range of 1 to 10%. The nicotinic acid derivative or the 2-pyrazinecarboxylic acid derivative represented by the general formula (II) is added in a supplemental manner during the reaction, if necessary. In some cases, the reaction is accelerated by optionally adding metal ion.

The 3-hydroxy nitrogen-containing six-membered cyclic compound obtained by the cultivation and the reaction can be collected in accordance with ordinary methods for separation and purification such as extraction with solvent and chromatography.

The present invention has made it possible to conveniently produce the 3-hydroxy nitrogen-containing six-membered compound which is useful as an intermediate material for producing pharmaceuticals, from the nicotinic acid derivative or the 2-pyrazinecarboxylic acid derivative by utilizing the microorganism.

DESCRIPTION OF THE PREFERRED EMBODIMENTS

The present invention will be explained below with reference to Examples. However, the present invention may be modified in an ordinary manner conceivable by those skilled in the art in the technical field of the present invention provided that the gist the present invention is not exceeded.

EXAMPLE 1

*Rhodococcus rhodochrous* ATCC 14350 was inoculated into a liquid medium (400 mL) having a composition comprising 3.0 g/L of dipotassium hydrogenphosphate, 1.0 g/L of potassium dihydrogenphosphate, 4.0 g/L of 2-chloronicotinic acid, 10.0 g of sorbitol, 4.0 g/L of polypeptone, 0.5 g/L of magnesium sulfate heptahydrate, 0.01 g/L of manganese sulfate tetra- or pentahydrate, 20 mg/L of inositol, 20 mg/L of nicotinic acid amide, 20 mg/L of thiamin hydrochloride, 20 mg/L of calcium pantothenate, and water (pH 7.0). The microorganism was aerobically cultivated at 30° C. for 96 hours. An obtained culture liquid was centrifuged to collect microbial cells which were then washed with an aqueous solution of 50 mM potassium chloride. A potassium phosphate buffer (25 mM, pH 7.5) containing 15 g/L of nicotinic acid was added to the obtained microbial cells to provide a total amount of 400 mL, followed by a reaction at 30° C. for 24 hours under an aerobic condition. Upon completion of the reaction, 3-hydroxypyridine was produced and accumulated in an amount of 0.85 g/L.

EXAMPLE 2

*Rhodococcus rhodochrous* ATCC 19150 was inoculated into a liquid medium (100 mL) having a composition comprising 3.0 g/L of dipotassium hydrogenphosphate, 1.0 g/L of potassium dihydrogenphosphate, 4.0 g/L of 2-chloronicotinic acid, 10.0 g of saccharose, 4.0 g/L of yeast extract, 0.5 g/L of magnesium sulfate heptahydrate, 0.01 g/L of manganese sulfate tetra- or pentahydrate, and water (pH 7.0). The microorganism was aerobically cultivated at 30° C. for 48 hours. An obtained culture liquid was centrifuged to collect microbial cells which were then washed with a potassium phosphate buffer (50 mM, pH 7.0). A potassium phosphate buffer (25 mM, pH 7.0) containing 15 g/L of nicotinic acid was added to the obtained microbial cells to provide a total amount of 100 mL, followed by a reaction at 30° C. for 24 hours under an aerobic condition. Upon completion of the reaction, 3-hydroxypyridine was produced and accumulated in an amount of 0.41 g/L.

EXAMPLE 3

The method for cultivation and reaction was carried out in the same manner as described in Example 2 except that a microbial strain of *Rhodococcus equi* ATCC 21329 was used. After 24 hours, 3-hydroxypyridine was produced and accumulated in an amount of 0.22 g/L.

EXAMPLE 4

The method for cultivation and reaction was carried out in the same manner as described in Example 2 except that a microbial strain of Rhodococcus sp. MCI 2956 was used. After 24 hours, 3-hydroxypyridine was produced and accumulated in an amount of 0.24 g/L.

EXAMPLE 5

The method for cultivation was carried out in the same manner as described in Example 2 except that a microbial strain of Rhodococcus sp. IFO 13161 was used. An obtained culture liquid was centrifuged to collect microbial cells which were then washed with a potassium phosphate buffer (50 mM, pH 7.0). A potassium phosphate buffer (25 mM, pH 7.0) containing 15 g/L of sodium nicotinate and 20 mM magnesium sulfate heptahydrate was added to the obtained microbial cells to provide a total amount of 100 mL, followed by a reaction at 30° C. for 24 hours under an aerobic condition. After 24 hours, 3-hydroxypyridine was produced and accumulated in an amount of 0.14 g/L.

EXAMPLE 6

*Rhodococcus rhodochrous* ATCC 14350 was inoculated into a liquid medium (100 mL) having a composition comprising 3.0 g/L of dipotassium hydrogenphosphate, 1.0 g/L of potassium dihydrogenphosphate, 6.0 g/L of sodium nicotinate, 10.0 g of sorbitol, 4.0 g/L of polypeptone, 0.5 g/L of magnesium sulfate heptahydrate, 0.01 g/L of manganese sulfate tetra- or pentahydrate, and water (pH 7.0). The microorganism was aerobically cultivated at 30° C. for 90 hours. An obtained culture liquid was centrifuged to collect microbial cells which were then washed with a potassium phosphate buffer (50 mM, pH 7.0). A potassium phosphate buffer (25 mM, pH 7.5) containing 15 g/L of nicotinic acid was added to the obtained microbial cells to provide a total amount of 100 mL, followed by a reaction at 30° C. for 24 hours under an aerobic condition. Upon completion of the reaction, 3-hydroxypyridine was produced and accumulated in an amount of 0.11 g/L.

EXAMPLE 7

*Serratia plymuthica* IAM 13543 was inoculated into a liquid medium (30 mL) having a composition comprising 3.0 g/L of dipotassium hydrogenphosphate, 1.0 g/L of potassium dihydrogenphosphate, 3.0 g/L of 2-chloronicotinic acid, 10.0 g of sorbitol, 4.0 g/L of polypeptone, 0.12 g/L of magnesium sulfate heptahydrate, 20 ppm of inositol, 20 ppm of thiamine hydrochloride and water (pH 7.0). The microorganism was aerobically cultivated at 28° C. for 72 hours. An obtained culture liquid was centrifuged to collect microbial cells which were then washed with a potassium phosphate buffer (50 mM, pH 7.0). A potassium phosphate buffer (25 mM, pH 7.5) containing 15 g/L of nicotinic acid was added to the obtained microbial cells to provide a total amount of 3 mL, followed by a reaction at 30° C. for 10 hours under an aerobic condition. Upon completion of the reaction, 3-hydroxypyridine was produced and accumulated in an amount of 1.24 g/L.

EXAMPLE 8

*Serratia marcescens* IAM 12142 was cultivated and the reaction was performed in the same manner as described in Exmaple 7. Upon completion of the reaction, 3-hydroxypyridine was produced and accumulated in an amount of 1.22 g/L.

What is claimed is:

1. A method for producing a 3-hydroxy nitrogen-containing six-membered cyclic compound represented by the following general formula (I):

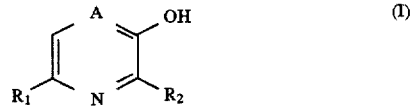

wherein $R_1$ and $R_2$ independently represent hydrogen atom, halogen atom, hydroxyl group, amino group, carboxyl group, cyano group, oxime group, or alkyl group having a number of carbon atom or atoms of 1 to 5 respectively, and A represents carbon atom or nitrogen atom, the method comprising the step of:

allowing microbial cells of a microorganism and/or a preparation obtained from the microbial cells to act on a nicotinic acid derivative or a 2-pyrazinecarboxylic acid derivative represented by the following general formula (II):

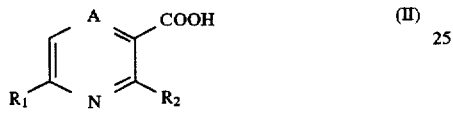

wherein $R_1$, $R_2$, and A are synonymous with those defined in the formula (I), the microbial cells and/or the preparation obtained from the microbial cells having an ability to perform hydroxylation of the nicotinic acid derivative or the 2-pyrazinecarboxylic acid derivative accompanied by decarboxylation of carboxyl group.

2. The method according to claim 1, wherein A is carbon atom.

3. The method according to claim 1, wherein each of $R_1$ and $R_2$ is hydrogen atom or halogen atom.

4. The method according to claim 1, wherein each of $R_1$ and $R_2$ represents hydrogen atom, and A represents carbon atom.

5. The method according to claim 1, wherein $R_1$ represents halogen atom, $R_2$ represents hydrogen atom, and A represents carbon atom.

6. A method for producing a 3-hydroxy nitrogen-containing six-membered cyclic compound represented by the following general formula (I):

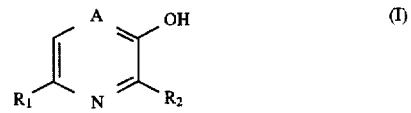

wherein $R_1$ and $R_2$ independently represent hydrogen atom, halogen atom, hydroxyl group, amino group, carboxyl group, cyano group, oxime group, or alkyl group having 1 to 5 carbon atoms, and A represents carbon atom or nitrogen atom, the method comprising the step of:

allowing microbial cells and/or a preparation obtained from microbial cells to act on a nicotinic acid derivative or a 2-pyrazinecarboxylic acid derivative represented by the following general formula (II):

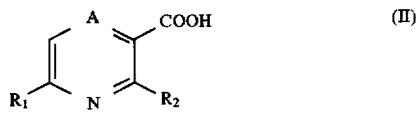

wherein $R_1$, $R_2$, and A have the same meanings as defined in the formula (I), the microbial cells and/or the preparation obtained from the microbial cells having an ability to perform hydroxylation of the nicotinic acid derivative or the 2-pyrazinecarboxylic acid derivative accompanied by decarboxylation of carboxyl group, wherein the microbial cells belong to the genus Rhodococcus or the genus Serratia.

* * * * *